US008530440B2

(12) United States Patent
Siegfried et al.

(10) Patent No.: US 8,530,440 B2
(45) Date of Patent: Sep. 10, 2013

(54) DSRNA DELIVERY COMPOSITION AND METHODS OF USE

(75) Inventors: Blair Siegfried, Lincoln, NE (US); Murugesan Rangasamy, Indianapolis, IN (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 13/099,968

(22) Filed: May 3, 2011

(65) Prior Publication Data

US 2011/0268691 A1    Nov. 3, 2011

Related U.S. Application Data

(60) Provisional application No. 61/330,726, filed on May 3, 2010.

(51) Int. Cl.
*C12N 15/11*    (2006.01)
*C07H 21/04*    (2006.01)

(52) U.S. Cl.
USPC ........................................ 514/44 A; 536/24.5

(58) Field of Classification Search
USPC ........................................ 514/44 A; 536/24.5
See application file for complete search history.

(56) References Cited

U.S. PATENT DOCUMENTS 7,812,219 B2 * 10/2010 Baum et al. .................. 800/279
2007/0065476 A1 *  3/2007 Sexton et al. ................. 424/410
2009/0285784 A1 * 11/2009 Raemaekers et al. ........ 424/93.2

OTHER PUBLICATIONS

Baum et al. (Nature Biotechnology 11: 1322-1326, 2007).*
Marrone et al. J. Econ. Entom., 1985, 78:290-293.*
Nowatski et al., Effect of *Bacillus thuringiensis* cry3Bb1 Protein on Feeding Behavior and Longevity of Adult Western Corn Rootworms (Coleoptera: Chrysomelidae), 2006, Journal of Economic Entomology, pp. 927-930, vol. 99, No. 3.
Hammond et al., "Corn Rootworm Management", The Ohio State University Extension Fact Sheet Agriculture and Natural Resources, 2009, pp. 1-4.
Alves et al., "RNA Interference as a Method for Target-Site Screening in the Western Corn Rootworm, *Diabrotica virgifera virgifera*", Journal of Insect Science, 2010, pp. 1-16, vol. 10.
Baum et al., "RNA Interference Technology for Corn Rootworm Control", Entomological Society of America Annual Meeting, Indianapolis, Indiana, Dec. 13-16, Dec. 15, 2009.
Bautista et al., "RNA Interference-Mediated Knockdown of a Cytochrome P450, CYP6BG1, from the Diamondback Moth, *Plutella xyostella*, Reduces Larval Resistance to Permethrin", Insect Biochemistry and Molecular Biology, 2009, pp. 38-46, vol. 39.
Belles et al., "RNAi in vivo and Functional Genomics in Insects", Annual Review of Entomology, 2010, pp. 111-128, vol. 55.
Beyenbach et al., "The V-Type H+ ATPase: Molecular Structure and Function, Physiological Roles and Regulation", The Journal of Experimental Biology, 2006, pp. 577-589, vol. 209.

Fire et al., "Potent and Specific Genetic Interference by Double-Stranded RNA in *Caenorhabditis elegans*", Nature, 1998, pp. 806-811, vol. 391.
Graf et al., "Purification and Properties of a Cytosolic V1-ATPase", The Journal of Biological Chemistry, 1996, pp. 20908-20913, vol. 271.
Jackson, "*Diabrotica* spp.", in Singh and Moore (Eds), Handbook of Insect Rearing vol. 1, 1985, pp. 237-254, Elsevier Publishers, Amsterdam, The Netherlands.
Levine et al., "Adaptation of the Western Corn Rootworm, *Diabrotica virgifera virgifera* Le Conte (Coleoptera: Chrysomelidae) to Crop Rotation: Evolution of a New Strain in Response to a Cultural Management Practice", American Entomologist, 2002, pp. 94-107, vol. 48.
Mao et al., "Silencing a Cotton Bollworm P450 Monooxygenase Gene by Plant-Mediated RNAi Impairs Larval Tolerance of Gossypol", Nature Biotechnology, 2007, pp. 1307-1313, vol. 25.
Meinke et al., "Adult Susceptibility of Nebraska Western Corn Rootworm (Coleoptera: Chrysomelidae) Populations to Selected Insecticides", Journal of Economic Entomology, 1998, pp. 594-600, vol. 91.
Meister et al., "Mechanisms of Gene Silencing by Double-Stranded RNA", Nature, 2004, pp. 343-349, vol. 431.
Merzenforfer et al., "The Multigene Family of the Tobacco Hornworm V-ATpase: Novel Subunits a , C, D, H, and Putative Isoforms", Biochimica et Biophysica Acta, 2000, pp. 369-379, vol. 1467.
Metcalf et al., "Implications and Prognosis of Resistance to Insecticides" in Georghiou, Saito (Eds), Pest Resistance to Pesticides, 1983, pp. 703-733, Plenum Press New York.
Miota et al., "Mechanisms of Methyl and Ethyl Parathion Resistance in the Western Corn Rootworm (Coleoptera: Chrysomelidae)", Pesticide Biochemistry and Physiology, Aug. 15, 1998, pp. 39-52, vol. 61, Issue 1.
Nishi et al., "The Vacuolar (H+)-ATPases—Nature's Most Versatile Proton Pumps", Nature Reviews Molecular Cell Biology, 2002, pp. 94-103, vol. 3.
O'Neal et al., "Predicting Western Corn Rootworm (Coleoptera: Chrysomelidae) Larval Injury to Rotated Corn with Pherocon AM Traps in Soybeans", Journal of Economic Entomology, 2001, pp. 98-105, vol. 94.
Parami et al., "Stability and Persistance of Aldrin and Methyl-Parathion Resistance in Western Corn Rootworm Populations (Coleoptera: Chyrsomelidae)", Crop Protection, 2006, pp. 269-274,vol. 25.
Price et al., "RNAi-Mediated Crop Protection Against Insects", Trends in Biotechnology, 2008, pp. 393-400, vol. 26.
Rice, "Transgenic Rootworm Corn: Assesing Potential Agronomic, Economic, and Enviromental Benefits", online, Plant Health Progress, 2003.

(Continued)

*Primary Examiner* — Brian Whiteman
(74) *Attorney, Agent, or Firm* — Thompson Coburn LLP (57) ABSTRACT

The present invention provides for compositions comprising a cucurbitacin bait for stimulating insect feeding and a dsRNA—such as for eliciting RNAi mediated gene silencing in an insect. The present invention also provides for methods of delivering a dsRNA molecule to an insect, inhibiting protein expression in an insect, and killing an insect by providing a dsRNA molecule.

22 Claims, 7 Drawing Sheets

(56) References Cited

OTHER PUBLICATIONS

Sappington et al., "Coordinated *Diabrotica* Genetics Research: Accelerating Progress on an Urgent Insect Pest Problem", American Entomologist, 2006, pp. 90-97, vol. 52.

Sidahmed et al. "Endogenous Antiviral Mechanisms of RNA Interference: A Comparative Biology Perspective", Methods in Molecular Biology, 2010, pp. 3-19.

Siegfried et al., "Baseline Susceptibility of Western Corn Rootworm (Coleoptera: Chrysomelidae) to Cry3Bb1 *Bacillus thuringiensis* Toxin", Journal of Economic Entomology, 2005, pp. 1320-1324, vol. 98.

Tallamy et al., "Western Corn Rootworm, Cucurbits and Cucurbitacins (Chapter 4)", Western Corn Rootworm: Ecology and Management, 2005, pp. 67-93.

Timmons et al., "Ingestion of Bacterially Expressed dsRNAs Can Produce Specific and Potent Genetic Interference in *Caenorhabditis elegans*", Gene, 2001, pp. 103-112, vol. 263.

Turner et al., "RNA Interference in the Light Brown Apple Moth, *Epiphyas postvittana* (Walker) Induced by Double-Stranded RNA Feeding", Insect Molecular Biology, 2006, pp. 383-391, vol. 15.

Walshe et al., "Prolonged Gene Knockdown in the Tsetse Fly Glossina by Feeding Double-Stranded RNA", Insect Molecular Biology, 2009, pp. 11-19, vol. 18.

Whyard et al., "Ingested Double-Stranded RNAs Can Act as Species-Specific Insecticides", Insect Biochemistry and Molecular Biology, 2009, pp. 824-832, vol. 39.

Wieczorek et al., "Animal Plasma Membrane Energization by Proton-Motive V-ATPases", Bioessays, 1999, pp. 637-648, vol. 21.

Zhou et al., "Characterization of General Esterases from Methyl Parathion-Resistant and -Susceptible Populations of Western Corn Rootworm (Coleoptera: Chrysomelidae)", Journal of Economic Entomology, Dec. 2003, pp. 1855-1863, vol./No. 96(6).

Zhou et al., "RNA Interference in the Termite *Reticulitermes flavipes* Through Ingestion of Double-Stranded RNA", Insect Biochemistry and Molecular Biology, 2008, pp. 805-815, vol. 38.

* cited by examiner

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: T7 polymerase promoter sequence

<400> SEQUENCE: 1
taatacgact cactataggg                                           20

<210> SEQ ID NO 2
<211> LENGTH: 13
<212> TYPE: DNA
<213> ORGANISM: Diabrotica virgifera

<400> SEQUENCE: 2
tattgtacag gtg                                                  13

<210> SEQ ID NO 3
<211> LENGTH: 11
<212> TYPE: DNA
<213> ORGANISM: Diabrotica virgifera

<400> SEQUENCE: 3
caatttccaa g                                                    11

<210> SEQ ID NO 4
<211> LENGTH: 21
<212> TYPE: DNA
<213> ORGANISM: Artificial Sequence
<220> FEATURE:
<223> OTHER INFORMATION: gfp primer

<400> SEQUENCE: 4
ggtgatgcta catacggaaa g                                         21

<210> SEQ ID NO 5
<211> LENGTH: 18
<212> TYPE: DNA
<213> ORGANISM: Artificial Sequence
<220> FEATURE:
<223> OTHER INFORMATION: gfp primer

<400> SEQUENCE: 5
ttgtttgtct gccgtgat                                             18

```
<210> SEQ ID NO 6
<211> LENGTH: 667
<212> TYPE: DNA
<213> ORGANISM: Diabrotica virgifera

<400> SEQUENCE: 6
taatccagac agagaaggat ccgtttcaat tgtaggagcc gtatcacctc ctggtggtga      60
tttctcagat cctgttacca ctgctactct tggtattgta caggtgttct ggggtttgga     120
caagaaactt gcccaacgta agcacttccc ttcagtagac tggcttggat catattccaa     180
atatttaaga gcattggacg acttttatga caaaaacttc caagagttta ttcctcttag     240
aaccaaagtt aaggaaattc ttcaggaaga agatgatcta gccgaaattg tgcagctggt     300
aggtaaagca tctctggcag aaacggacaa aatcaccttg gaaattgcca ggcttcttaa     360
agaagatttc ttgcaacaaa actcatactc ttcttatgac agattctgtc cattctataa     420
aactgtcggt atgttgagaa acatgatcgg tttgtacgac atggcgagac acgctgtaga     480
atcaaccgca caatcagaaa ataagatcac ttggaacgta ataagagatt caatgagtgg     540
aattttatat caacttagca gtatgaaatt taaggatccc gtaaaagatg gtgaagctaa     600
aatcaaggca gattttgatc aattatatga agatattcag caggccttca gaaacttaga     660
agattaa                                                              667

<210> SEQ ID NO 7
<211> LENGTH: 301
<212> TYPE: DNA
<213> ORGANISM: Diabrotica virgifera

<400> SEQUENCE: 7
ggggtttgga caagaaactt gcccaacgta agcacttccc ttcagtagac tggcttggat      60
catattccaa atatttaaga gcattggacg acttttatga caaaaacttc caagagttta     120
ttcctcttag aaccaaagtt aaggaaattc ttcaggaaga agatgatcta gccgaaattg     180
tgcagctggt aggtaaagca tctctggcag aaacggacaa aatcaccttg gaaattgcca     240
ggcttcttaa agaagatttc ttgcaacaaa actcatactc ttcttatgac agattctgtc     300
c                                                                    301

<210> SEQ ID NO 8
<211> LENGTH: 1799
<212> TYPE: DNA
<213> ORGANISM: Diabrotica virgifera

<400> SEQUENCE: 8
acacacgcta taatttgatc tttgatcggt cacaatgttg tagtgttttt agtttattgt      60
gcctcgaaga gacaaaatct aaccatggct catgtggtgc aactagcgga aggaaaaatt     120
tctggaggca ctaggacaga tctcaatggg gataagtttc attcgttttt atgtatccca     180
tacggaaaag ctccagtagg cgacctacgg tttaaggcgc cattacctgt tgaaccatgg     240
gaaggggtaa acaagttat cacagaagac aaaacgccat tccagaagaa cattgttctg     300
aaggaatata ctggagaaga agattgcttg tctcttcatg tatttacaaa gaaacttccc     360
catgaagaat ccaaactgaa acctgtgatg gtgtacattc atggaggagg ttttataatg     420
ggatctcacg aaactacgat gtatggtcca gaataccta tgactgaaga catagttctc     480
gtaagcatca cttaccgagt tggtctactg gttttcctta gtatagaaga cgaatcactg     540
gacgttcctg gaaatgcagg tctaaaagat caagtactgg ctttaaagtg ggtccagcga     600
```

```
aacataagaa atttcaatgg agatcccaat aacattacca tatttggaga aagtgcggga    660
ggggcatctg ttgaattttt gctgttatct ccttcagcca aaggtttatt tcataaagcc    720
atacttcaga gcgggtcgac tttaaatcca tggactctta aaaactcccc agcaactgag    780
tttgctgagt ttaccaaact acataacttg cctgatattg acattttgaa aagcttgagg    840
cgtatgactg ttagggagct gtacgatcaa caaaatcaat atattaagtc taagaagcta    900
tttgtagatt tcggtctaat aaccccagtg atagaaaaac ccaacccaac agcattttg     960 acagagaaac ctatcgacat catccagtca gggaaataca acaatgtgcc agtgataatg   1020
ggttacaccg acagtgaagg tcttcttcta gacttcttgt cggcacttgg aatgaacggg   1080
gcaaaagagg gagaagatat acctattgag cagatactac catacgagac aaatttaaca   1140
gatgcacaac aagtcaaacg attagttgaa aagttaagaa attttatcg tccagaagct    1200 gatccggttg gacgaattaa tttatctacg gatgccttgt ttgcggctgg aataatcact   1260
tctgcaaaaa atcaagcgaa agtgtcaaag aaccctgtat attttatag attttcattg    1320 gacgcaggcc ttaacatgct gaagaaaatg gtgaatgata cacgtccagg agcttgtcac   1380
ggggatgaac tgggatacct atttaaaaac cttttgacaa cagacattgg agatgaagat   1440
aaaacttata tacatcgaat ggtaacacta tggacaaact ttgccaaata tggaaatcca   1500
acaccaccag gaaataatct aaacattgaa tggaagccga tacagaatgg tcagttgaat   1560
ttcttagata ttggaaaaca actaaagatg gatgtgaatc cagacgctga caggatgaaa   1620
atttggaatg agctttacca gtgtaatcca ctgacagcta atattaaat  ttgtttgcaa   1680 caactctcag aaatacatgt tattatattt ttatattata aaaatattt  atatcatatt   1740 ttaagactat acgaataaaa ctgattactt tattttaaaa taaagttact acacaaaaa   1799
```

<210> SEQ ID NO 9
<211> LENGTH: 267
<212> TYPE: DNA
<213> ORGANISM: Diabrotica virgifera

<400> SEQUENCE: 9

```
gctatttgta gatttcggtc taataacccc agtgatagaa aaacccaacc caacagcatt     60
tttgacagag aaacctatcg acatcatcca gtcagggaaa tacaacaatg tgccagtgat    120
aatgggttac accgacagtg aaggtcttct tctagacttc ttgtcggcac ttggaatgaa    180
cggggcaaaa gagggagaag atatacctat tgagcagata ctaccatacg agacaaattt    240
aacagatgca caacaagtca aacgatt                                        267
```

<210> SEQ ID NO 10
<211> LENGTH: 20
<212> TYPE: DNA
<213> ORGANISM: Artificial Sequence
<220> FEATURE:
<223> OTHER INFORMATION: WCR actin primer

<400> SEQUENCE: 10

```
gttggattct ggtgatggtg                                                 20
```

<210> SEQ ID NO 11
<211> LENGTH: 20
<212> TYPE: DNA
<213> ORGANISM: Artificial Sequence
<220> FEATURE:
<223> OTHER INFORMATION: WCR actin primer

<400> SEQUENCE: 11

-continued

```
ctctttctgc tgtggtggtg                                              20

<210> SEQ ID NO 12
<211> LENGTH: 25
<212> TYPE: DNA
<213> ORGANISM: Artificial Sequence
<220> FEATURE:
<223> OTHER INFORMATION: WCR vATPase primer

<400> SEQUENCE: 12
ggaagaagat gatctagccg aaatt                                        25

<210> SEQ ID NO 13
<211> LENGTH: 20
<212> TYPE: DNA
<213> ORGANISM: Artificial Sequence
<220> FEATURE:
<223> OTHER INFORMATION: WCR vATPase primer

<400> SEQUENCE: 13
ttgtccgttt ctgccagaga                                              20
```

DSRNA DELIVERY COMPOSITION AND METHODS OF USE

CROSS-REFERENCE TO RELATED APPLICATIONS

This application claims priority to U.S. Provisional Patent Application No. 61/330,726, filed May 3, 2010, and incorporated herein by reference in its entirety.

STATEMENT REGARDING FEDERALLY SPONSORED RESEARCH OR DEVELOPMENT

Not Applicable.
Incorporation of Sequence Listing
A Sequence Listing containing the file named "94788_SEQ LISTING_ST25.txt" which is (5664 bytes as measured in MS-Windows®) and created on May 3, 2011, is incorporated herein by reference in its entirety. The Sequence Listing contains SEQ ID NOs: 1-9.

INCORPORATION OF APPENDIX

An Appendix to the Specification titled "Appendix_Table_1.pdf" (97217 bytes as measured in MS-Windows®) is provided herewith and is herein incorporated by reference in its entirety.

BACKGROUND OF THE INVENTION

RNA interference (RNAi) has become an important tool for reverse functional genomics (Fire et al., 1998). RNAi is a naturally occurring defense mechanism that is highly conserved among eukaryotes. RNAi protects the genome against invention by mobile genetic elements, such as transposons, viruses, and other highly repetitive genomic sequences, and also to control the function of developmental programs in eukaryotic organisms (Sidahmed and Bruce, 2010). RNAi involves the cleavage of double-stranded RNA (dsRNA) by an RNaseIII-type enzyme called Dicer into small interfering RNAs (siRNA), that then direct sequence-specific, homology-dependent, post-transcriptional gene silencing by binding to its complementary RNA and triggering its elimination through degradation or by inducing translational inhibition (Fire et al., 1998; Meister and Tuschl, 2004). RNAi has widely been used to study function, regulation, and expression of gene cascades in both model and non-model insects from a variety of orders including Orthoptera, Dictyoptera, Isoptera, Hemiptera, Coleoptera, Neuroptera, Hymenoptera, Diptera, and Lepidoptera (Belles, 2010). Generally, these studies involve direct injection of dsRNA into various developmental stages. Only a few studies have involved feeding dsRNAs through artificial diets. Delivery of dsRNA by feeding was first demonstrated in 2001 in *Caenorhabditis elegans* (Timmons et al., 2001), but has since only been documented in a limited number of insect species such as brown apple moth larvae (*Epiphyas postvittana*; Turner et al., 2006), tsetse fly (*Glossina morsitans* morsitans; Walshe et al., 2009), termites (*Reticulitermes flavipes*; Zhou et al, 2008), diamondback moth larvae (*Plutella xylostella*; Bautista et al., 2009), pea aphid (*Aphis pisum*), tobacco horn worm (*Manduca sexta*), and red flour beetle (*Tribolium castaneum*) (Whyard et al., 2009).

The western corn rootworm (WCR), *Diabrotica virgifera virgifera* LeConte (Coleoptera: Chrysomelidae), is perhaps the most destructive insect pest of corn in the US corn belt (Sappington et al, 2006) and the costs of management and crop losses potentially exceed $1 billion (Rice, 2003). Managing corn rootworm has become increasingly difficult because of its sequential evolution of resistance to different insecticide classes (Meinke et al., 1998; Metcalf, 1983; Parimi et al., 2006; Siegfried et al., 2005) and cultural control practices such as crop rotation (Levine et al., 2002; O'Neal et al., 2001). Currently available rootworm management tools include transgenic corn hybrids expressing *Bacillus thuringiensis* (Bt) toxins such as Cry3Bb1, Cry34Ab1/Cry35Ab1 and mCry3A (United States Environmental Protection Agency 2005a; 2005b; 2006) and seed treatment with neonicotinoid insecticides.

The concept of using RNAi as a method of controlling insect pests is of commercial interest (Baum et al., 2007) and development of an efficient dsRNA delivery by feeding is a prerequisite for using RNAi in crop protection (Price and Gatehouse, 2008). RNAi has been shown to cause larval mortality of WCR in feeding assays using exposure to dsRNA of vacuolar-ATPase (vATPase) subunit A in artificial diet and to transgenic plants expressing dsRNA for this gene which exhibited reduced root injury from larval feeding (Baum et al., 2007). Maintaining WCR larvae on artificial diets (Nowatzki et al., 2006), however, is limited by microbial contamination limiting larval growth to no more than about 7 days. As WCR adults feed extensively on leaf tissues, pollen, tassels, and silk, the effect of dsRNA feeding on WCR adults requires further examination.

SUMMARY OF THE INVENTION

The present invention provides for compositions comprising a cucurbitacin bait for stimulating insect feeding and a dsRNA—such as for eliciting RNAi mediated gene silencing in an insect—and methods for using such compositions. Certain embodiments of the invention provide for a composition for delivering a dsRNA molecule to an insect comprising a cucurbitacin bait and at least one dsRNA molecule. In certain embodiments, the dsRNA elicits an RNAi response in the insect. In certain embodiments, the composition comprises at least two dsRNA molecules of different sequences.

Certain embodiments of the invention provide for a method of delivering a dsRNA molecule to an insect comprising providing the insect with a composition comprising a cucurbitacin bait and at least one dsRNA molecule to feed upon. In certain embodiments, the insect is selected from the group consisting of western corn rootworm, *Diabrotica balteata* LeConte, banded cucumber beetle, *Diabrotica barberi* Smith and Lawrence, northern corn rootworm, *Diabrotica undecimpunctata* howardi Barber, southern corn rootworm, and *Diabrotica speciosa*. In certain embodiments, the insect is a western corn rootworm.

Certain embodiments of the invention provide for a method of inhibiting the expression of one or more proteins in an insect. Such method comprises identifying one or more proteins to be inhibited, designing and synthesizing at least one dsRNA molecule to inhibit protein expression by eliciting an RNAi response in the insect, preparing a composition comprising a cucurbitacin bait and the at least one dsRNA molecule, and providing the composition to the insect to feed upon.

Certain embodiments of the invention provide for a method of producing a composition for delivering a dsRNA molecule to an insect comprising combining a cucurbitacin bait and at least one dsRNA molecule.

DETAILED DESCRIPTION

Headings are provided herein solely for ease of reading and should not be interpreted as limiting.

Concentrations, amounts, and other numerical data may be presented here in a range format (e.g., from 5% and 20%). It is to be understood that such range format is used merely for convenience and brevity and—unless explicitly stated otherwise—should be interpreted flexibly to include not only the numerical values explicitly recited as the limits of the range, but also to include all the individual numerical values or sub-ranges encompassed within that range, as if each numerical value and sub-range is explicitly recited. For example, a range of from 5% to 20% should be interpreted to include numerical values such as, but not limited to 5%, 5.5%, 9.7%, 10.3%, 15%, etc., and sub-ranges such as, but not limited to 5% to 10%, 10% to 15%, 8.9% to 18.9%, etc., in addition to any other values, sub-ranges, etc., provided for illustrative purposes.

As used herein, it is understood that "a dsRNA molecule" refers to a dsRNA molecule of a particular nucleic acid sequence and that in administering a particular dsRNA molecule, multiple copies of the molecule will generally be provided.

I. Description of the Sequence Listing

SEQ ID NO:1—T7 polymerase promoter sequence.
SEQ ID NO:2—primer for putative WCR vATPase subunit A clone.
SEQ ID NO:3—primer for putative WCR vATPase subunit A clone.
SEQ ID NO:4—primer for gfp gene negative control.
SEQ ID NO:5—primer for gfp gene negative control.
SEQ ID NO:6—Partial cDNA sequence for *Diabrotica virgifera* virgifera vATPase.
SEQ ID NO:7—Subsequence of SEQ ID NO:6.
SEQ ID NO:8—*Diabrotica virgifera* virgifera EST3 cDNA sequence.
SEQ ID NO:9—Subsequence of SEQ ID NO:8.
SEQ ID NO:10—primer for the housekeeping gene WCR actin.
SEQ ID NO:11—primer for the housekeeping gene WCR actin.
SEQ ID NO:12—primer for the putative WCR vATPase.
SEQ ID NO:13—primer for the putative WCR vATPase.

II. Overview

The present invention provides for the use of RNAi to cause mortality in certain insects through feeding of compositions comprising dsRNA. The "RNAi response" involves the cleavage of double-stranded RNA (dsRNA) by an RNaseIII-type enzyme called Dicer into small interfering RNAs (siRNA), that then direct sequence-specific, homology-dependent, post-transcriptional gene silencing by binding to its complementary RNA and triggering its elimination through degradation or by inducing translational inhibition (Fire et al., 1998; Meister and Tuschl, 2004).

In an illustrative example of one embodiment of the invention, western corn rootworm adults were fed a dsRNA treated artificial diet containing the Diabroticinae feeding stimulant containing cucurbitacins. It was discovered that the addition of cucurbitacins to the dsRNA treated artificial diet resulted in an efficient dsRNA delivery method for WCR adults. Thus, the present dsRNA delivery composition and method may provide a useful tool for studying the effects of RNAi on certain insects including western corn rootworm adults, while circumventing the inherent difficulties associated with maintaining insect larvae on artificial diets. The invention, however, is not limited to only adult insects as certain immature insects will also feed on compositions of the invention.

III. Cucurbitacins

Cucurbitacins are a group of non-volatile, highly oxygenated tetracyclic triterpenes produced in at least some tissues of all members of the Cucurbitaceae plant family. Cucurbitacins are phagostimulants for both adults and larvae of several luperine species in the subtribes Aulocophorina and Diabroticina of the Crysomelid family (Tallamy et al., 2005). Representative examples of insects in which cucurbitacins stimulate feeding include western corn rootworm, *Diabrotica balteata* LeConte, the banded cucumber beetle, *Diabrotica barberi* Smith and Lawrence, the northern corn rootworm, *Diabrotica undecimpunctata* howardi Barber, the southern corn rootworm, and *Diabrotica speciosa*. For example, a known cucurbitacin bait INVITE EC™ (Florida Food Products Inc., Eustis, Fl.) has been shown to stimulate WCR adults feeding on an artificial diet containing Bt toxins (Nowatzki et al., 2006).

IV. Composition for Delivering dsRNA Molecule(s) to an Insect

Certain embodiments of the invention provide for an artificial diet comprising a composition for delivering a dsRNA molecule to an insect. The composition comprises a cucurbitacin bait (also referred to herein as a feeding stimulant) and at least one dsRNA molecule. In certain embodiments, the composition comprises from about 5% to about 50%, or from about 5% to about 40%, or from about 5% to about 25%, or from about 5% to about 15% of the cucurbitacin bait. In certain embodiments, the composition comprises about 10% of the cucurbitacin bait.

The composition may comprise additional components such as are known in the field to formulate artificial diets for insects. For example, in certain embodiments, the composition comprises agar or an equivalent component that will thicken or solidify the composition. In certain embodiments, the composition comprises agar at a concentration of at least about 4%. In certain embodiments, the composition includes some or all of methyl paraben, sorbic acid, streptomycin (to minimize fungal and bacterial contamination), and honey.

The RNAi response leads to sequence-specific, homology-dependent, post-transcriptional gene silencing. This response may be elicited by certain dsRNA molecules, especially those that have been designed with specific genes as target, such as by using the cDNA sequence of the genes as a template. Thus, in certain embodiments, the dsRNA molecule of the composition is capable of eliciting an RNAi response in an insect. In certain embodiments, the composition may comprise more than one dsRNA molecule of different sequences, such as more than one dsRNA molecule of different sequences designed to silence the same gene or more than one dsRNA molecule of different sequences designed to silence distinct genes.

One representative example of a dsRNA molecule useful in practicing the invention is a vATPase subunit-A dsRNA molecule designed to elicit an RNAi response. In certain embodiments, the vATPase subunit A-dsRNA molecule is designed using a partial cDNA sequence for *Diabrotica virgifera* virgifera vATPase as set forth in SEQ ID NO:6 as a template for dsRNA synthesis. In certain embodiments, the vATPase subunit A-dsRNA molecule is designed using the sequence as set forth in SEQ ID NO:7 as a template for dsRNA synthesis.

Another representative example of a dsRNA molecule useful in practicing the invention is a DvvEST3 dsRNA molecule designed to elicit an RNAi response. In certain embodiments, the DvvEST3 dsRNA molecule is designed using a cDNA sequence for *Diabrotica virgifera* virgifera DvvEST3 as set forth in SEQ ID NO:8 as a template for dsRNA synthesis. In certain embodiments, the DvvEST3 dsRNA molecule is designed using the sequence as set forth in SEQ ID NO:9 as a template for dsRNA synthesis. Appendix: Table 1.

Certain embodiments of the invention provide for a method of producing a composition for delivering a dsRNA molecule to an insect comprising combining a cucurbitacin bait and at least one dsRNA molecule. For example, in certain embodiments, the cucurbitacin bait and dsRNA molecule(s) may be combined by preparing an artificial insect diet comprising the cucurbitacin bait and adding a solution of the dsRNA molecule(s).

Prior to preparing the composition, certain proteins may be identified to target for inhibition via RNAi mediated gene silencing. At least one dsRNA molecule may be designed and synthesized for combination with a cucurbitacin bait.

V. Methods for Delivering a dsRNA Molecule to an Insect

Certain embodiments of the present invention provide for methods of delivering a dsRNA molecule to an insect by providing the insect with a composition comprising a cucurbitacin bait and at least one dsRNA molecule to feed upon. In certain embodiments, the insect is selected from the group consisting of western corn rootworm, *Diabrotica balteata* LeConte, the banded cucumber beetle, *Diabrotica barberi* Smith and Lawrence, the northern corn rootworm, *Diabrotica undecimpunctata* howardi Barber, the southern corn rootworm, and *Diabrotica speciosa*. In certain embodiments, the insect is a western corn rootworm.

As noted, dsRNA molecules may elicit an RNAi response in an insect and in certain embodiments, the dsRNA molecule of the method is one that elicits an RNAi response when fed to an insect. In certain embodiments, the method comprises providing more than one dsRNA molecule of different sequences, such as more than one dsRNA molecule of different sequences designed to silence the same gene or more than one dsRNA molecule of different sequences designed to silence distinct genes.

RNAi mediated gene silencing results in the inhibition of protein expression. Certain embodiments of the present invention provide for methods of inhibiting the expression of a protein in an insect. Such methods comprise the steps of: a) identifying one or more proteins to be inhibited; b) designing and synthesizing a dsRNA molecule to inhibit the protein by eliciting an RNAi response in the insect; c) preparing a composition comprising a cucurbitacin bait and the dsRNA molecule; and d) feeding the insect the composition. In certain embodiments, the insect is selected from the group consisting of western corn rootworm, *Diabrotica balteata* LeConte, the banded cucumber beetle, *Diabrotica barberi* Smith and Lawrence, the northern corn rootworm, *Diabrotica undecimpunctata* howardi Barber, the southern corn rootworm, and *Diabrotica speciosa*. In certain embodiments, the insect is a western corn rootworm.

In certain embodiments, the method comprises designing and synthesizing more than one dsRNA molecule of different sequences, such as more than one dsRNA molecule of different sequences designed to inhibit expression of the same protein or more than one dsRNA molecule of different sequences designed to inhibit expression of different proteins.

RNAi mediated gene silencing and the resultant inhibition of protein expression may lead to death of an insect. Certain embodiments of the present invention provide for methods of causing death of an insect. Such methods comprise the steps of: a) identifying one or more genes for RNAi gene silencing; b) designing and synthesizing a dsRNA molecule to silence the genes by eliciting an RNAi response in the insect; c) preparing a composition comprising a cucurbitacin bait and the dsRNA molecule; and d) feeding the insect the composition. In certain embodiments, the insect is selected from the group consisting of western corn rootworm, *Diabrotica balteata* LeConte, the banded cucumber beetle, *Diabrotica barberi* Smith and Lawrence, the northern corn rootworm, *Diabrotica undecimpunctata* howardi Barber, the southern corn rootworm, and *Diabrotica speciosa*. In certain embodiments, the insect is a western corn rootworm. In certain embodiments, the gene or genes selected to be targeted by the dsRNA molecule(s) for RNAi mediated gene silencing are genes know to be required for the insect to continue to live. In certain embodiments, the gene or genes selected to be targeted by the dsRNA molecule(s) for RNAi mediated gene silencing are what are known to those of skill in the art as housekeeping genes.

In certain embodiments, the method comprises designing and synthesizing more than one dsRNA molecule of different sequences, such as more than one dsRNA molecule of different sequences designed to inhibit expression of the same protein or more than one dsRNA molecule of different sequences designed to inhibit expression of different proteins.

Similarly, certain embodiments of the invention provide for delivering a dsRNA to an insect to elicit RNAi mediate gene silencing in order to screen or study gene function or to control a population of insects.

VI. Examples

The following disclosed embodiments are merely representative of the invention which may be embodied in various forms. Thus, specific structural, functional, and procedural details disclosed in the following examples are not to be interpreted as limiting.

Example 1

Materials and Methods

1. *Diabrotica*-specific dsRNA preparation.

Total RNA was extracted from WCR larval midguts using TRIzol® (Invitrogen, Carlsbad, Calif.) and one µg total RNA was used to synthesize cDNA using QuantiTect reverse transcription kit (Qiagen, Valencia, Calif.). The PCR templates for in vitro transcription of dsRNAs were amplified using gene-specific primers tailed with the T7 polymerase promoter sequence (TAATACGACTCACTATAGGG) (SEQ ID NO: 1). The primers for the putative WCR vATPase subunit A clone (accession number CN498337.1), 5'-(T7) TATTGTA-CAGGTG-3' (SEQ ID NO: 2) and 5'-(T7) CAATTTCCAAG-3' (SEQ ID NO: 3), amplified a 258 bp fragment. A non-specific negative control, gfr) gene (green fluorescence protein) was amplified from the pIZT/V5-His expression vector (Invitrogen, Carlsbad, Calif.) using gene specific primers, 5'-(T7) GGTGATGCTACATACGGAAAG-3' (SEQ ID NO: 4) and 5'-(T7) TTGTTTGTCTGCCGTGAT-3' (SEQ ID NO: 5), that amplified a 370 bp fragment. After confirming template sequence, the vATPase- and gfp-dsRNA were synthesized in vitro using MEGAscript high yield transcription kit (Applied Biosystems Inc., Foster City, Calif.) and purified using Rneasy Mini kit (Qiagen, Valencia, Calif.) following manufacture's protocol and stored at −20° C.

2. Insect Bioassays.

Artificial diet for WCR adults was prepared using a protocol modified from (Jackson, 1985) and (Nowatzki et al., 2006). The diet consisted of 10% INVITE EC™ (Florida Food Products, Eustis, Fla.) diluted in 4% agar, 0.32% methyl paraben, 0.12% sorbic acid, 0.16% streptomycin (to minimize fungal and bacterial contamination), and 16.6% honey. Baum et al. (2007) screened dsRNAs of 290 WCR genes and found 14 dsRNAs yielding an $LC_{50}$ value of $\leq 5.2$ ng/cm$^2$. The WCR larvae fed on diet containing vATPase-dsRNA subunit A at 52 ng/cm$^2$ showed dramatic reduction in transcript levels as early as 12 hours after ingestion. However, little or no effect was observed until 7 days of exposure even for the most active dsRNA for the putative COPI coatomer, β subunit at 0.52 ng/cm$^2$. Based on these concentrations required for gene silencing at the larval stage, we reasoned that feeding of adults with 500 and 1000 ng/diet plug may cause sufficient gene suppression and phenotypic response. Diet plugs were treated with 2 µl of water of vATPase-dsRNA or gfp-dsRNA at 500 or 1000 ng/plug. Newly emerged (0 to 2 days old) non-diapause WCR adults were purchased from Crop Characteristics Inc. (Farmington, Minn.), and fed with the artificial diet for 24 hours before setting up bioassays. The WRC adults confined in individual wells of bioassay trays (C-D International, Pitman, N.J.) and provided with freshly treated diet plugs on every third day. Adults were collected 24, 48, and 72 hours after treatment and stored at −20° C. For adult mortality studies, freshly treated diet plugs were provided until all beetles were dead. The feeding assays were conducted using a split-plot randomized complete block design with time as split plot five replications, 16 adults per replication for each treatment. The mortality means were analyzed using PROC MIXED procedure (SAS/STAT®, 2001).

3. Real-Time PCR and Western Blot Studies.

RT-PCR assays were performed using the 7500 Fast Real-Time PCR system (Applied Biosystems). The total RNA was extracted from individual WCR adults using TRizol (Invitrogen, Carlsbad, Calif.) and the cDNA was synthesized using QuantiTect reverse transcription kit (Quiagen). The gene expression analysis was performed using 40 two-step cycles for 20 seconds at 95° C. and 30 seconds at 65° C. as described in the suppliers protocol (Applied Biosystems, Foster City, Calif.). The primer designed for the house keeping gene WCR actin were 5'-GTTGGATTCTGGTGATGGTG-3' (SEQ ID NO: 10) and 5'-CTCTTTCTGCTGTGGTGGTG-3' (SEQ ID NO: 11) which amplified a 164 bp fragment and for the putative WCR vATPase were 5'GGAAGAAGAT-GATCTAGCCGAAATT-3' (SEQ ID NO: 12) and 5'-TTGTCCGTTTCTGCCAGAGA3' (SEQ ID NO: 13) which amplified a 67 bp fragment. The putative WCR vATPase expression was normalized to the WRC actin expression by the comparative CT method and percentage knockdown was calculated using 7500 Fast System SDS v 2.0 software (Applied Biosystems, Foster City, Calif.).

Protein expression was examined by Western blotting using rabbit anti-V-ATPase subunit A polyclonal antibody (GenScript Inc., Piscataway, N.J.). Total protein was extracted from the WCR adults using extraction buffer containing 300 mM mannitol, 3 mM Na-EDTA, 50 mM NaCl, 17 mM Tris-NaCl, 3 mM Mercaptoethanol and protease inhibitor cocktail (1 tablet/10 ml, Complete Mini, EDTA-Free, Roche Applied Science, Indianapolis, Ind.). The total protein concentrations were colorimetrically determined using BCA (bicinchoninic acid) protein assay reagent (Thermo Fisher Scientific, Rockford, Ill.). Proteins (50 µg) were separated by SDS-PAGE and transferred to a nitrocellulose membrane (BioRad, Hercules, Calif.) using transfer buffer (25 mM Tris and 192 mM glycine in 20% methanol) at 80 mA overnight at 4° C. The membrane was blocked with 5% nonfat dry milk in TTBS (15 mM Tris/HCL, 150 mM NaCL, pH 7.5, 0.05% Tween 20) for 2 hours at room temperature and then incubated with rabbit anti-V-ATPase subunit A polyclonal antibody for 5 hours at room temperature. Subsequently the membrane was incubated for 2 hours with the anti-rabbit IgG-alkaline phosphatase secondary antibody (1:10,000 v/v, Sigma-Aldrich, St. Louis, Mo.) and alkaline phosphatase activity was developed using SIGMAFAST BCIP/NBT (5-bromo-4-chloro-3-indolyl phosphate/nitro blue tetrazolium (Sigma-Aldrich) as a substrate.

Results.

1. vATPase Knockdown in dsRNA-Fed WCR Adults.

Figure 1:
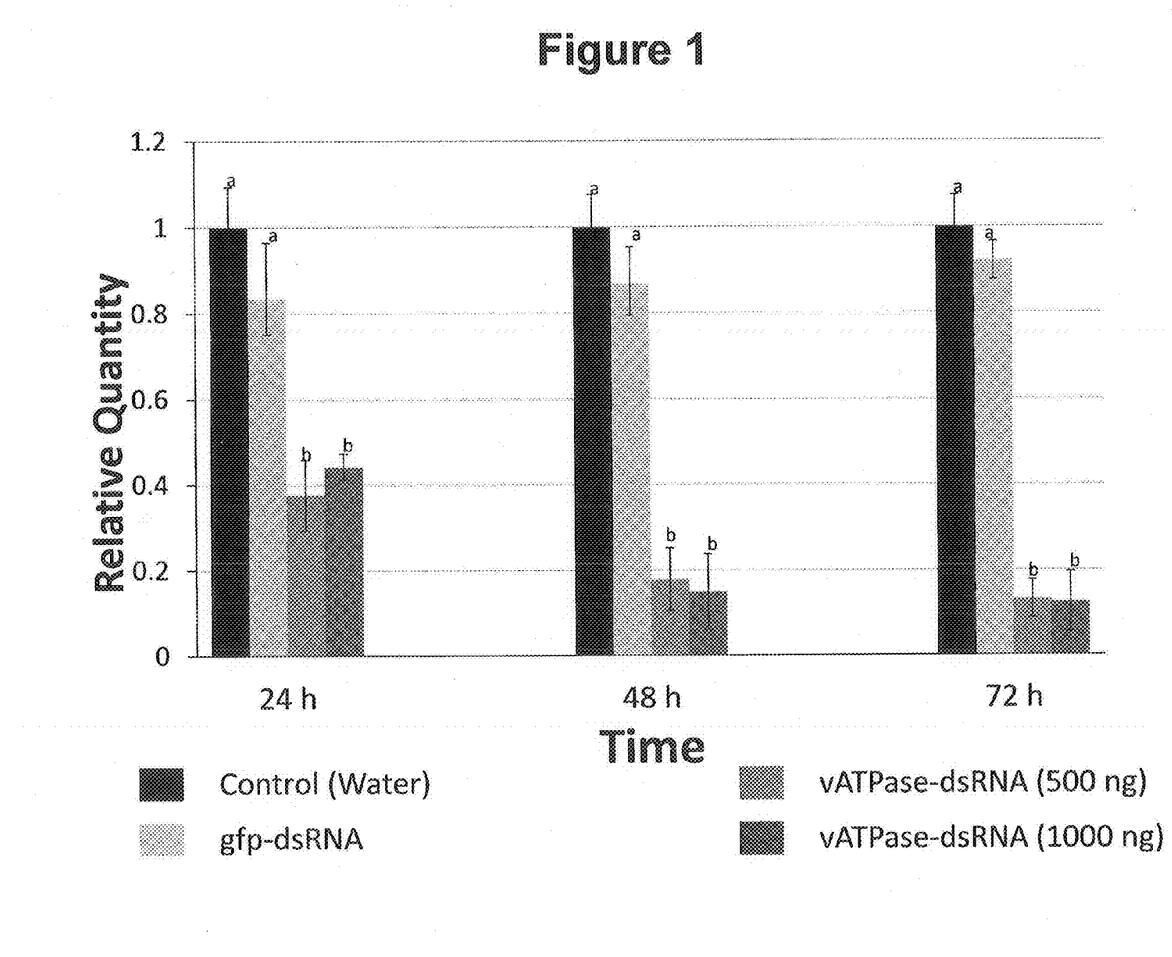
FIG. 1 shows the relative quantity (RQ) of the putative vATPase transcripts normalized to the WCR actin levels in dsRNA-fed WCR adults. The transcript levels of vATPase in control adults were set to 1, the relative expression levels in dsRNA-fed adults were determine with respect to control. Different letters (a, b) indicate significantly reduced transcript levels compared to controls. The error bars shown represent RQ-minimum and RQ-maximum at 95% confidence level.

WCR adults fed on artificial diet treated with vATPase-dsRNA showed a significant reduction in vATPase transcript levels at 24, 48, and 72 hours after feeding compared to control treatments in which adults were fed either water-treated diet or diet treated with gfp-dsRNA at 500 and 1000 ng concentrations ($p<0.01$, FIG. 1). No significant difference was observed between two vATPase-dsRNA concentrations used.

2. Western Analysis of v-ATPase Expression in dsRNA-Fed WCR Adults.

Figure 2:
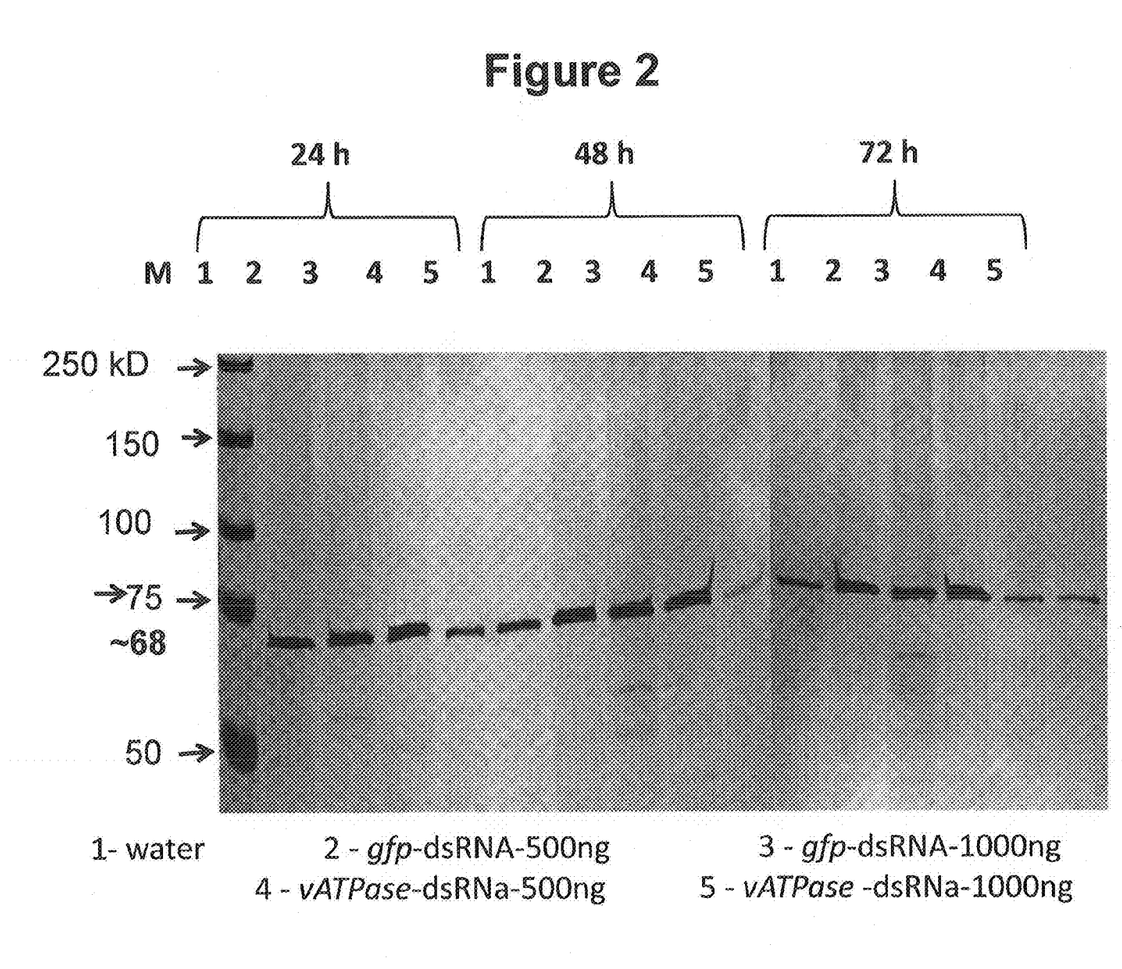
FIG. 2 shows the detection of V-ATPase subunit A in dsRNA fed and control WCR adults. Western blots of total protein were probed with a polyclonal antibody against V-ATPase subunit A.
Figure 3:
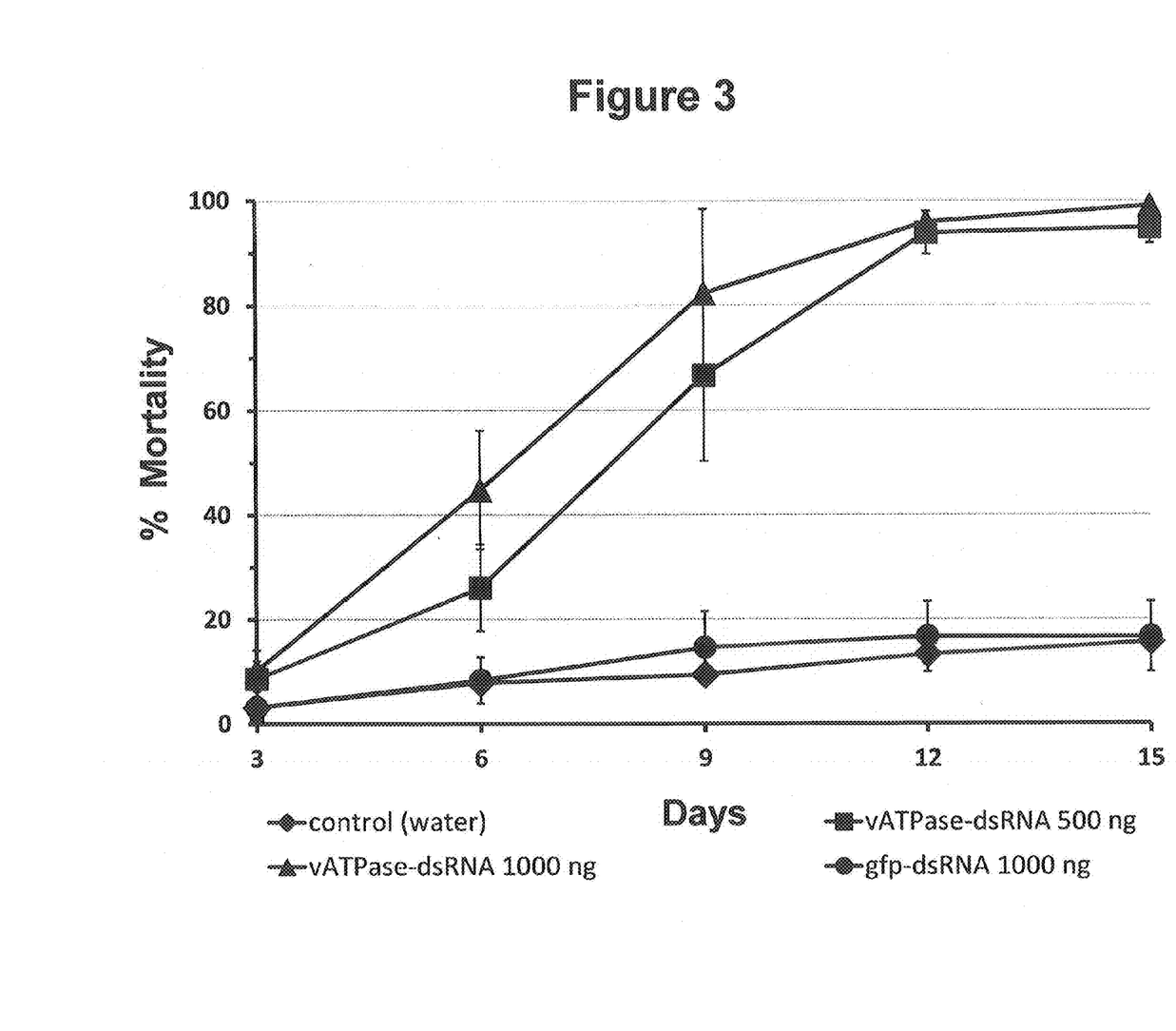
FIG. 3 shows mortality of WCR adults fed on diet treated with gfp- and vATPase-dsRNA and water.
Figure 4:
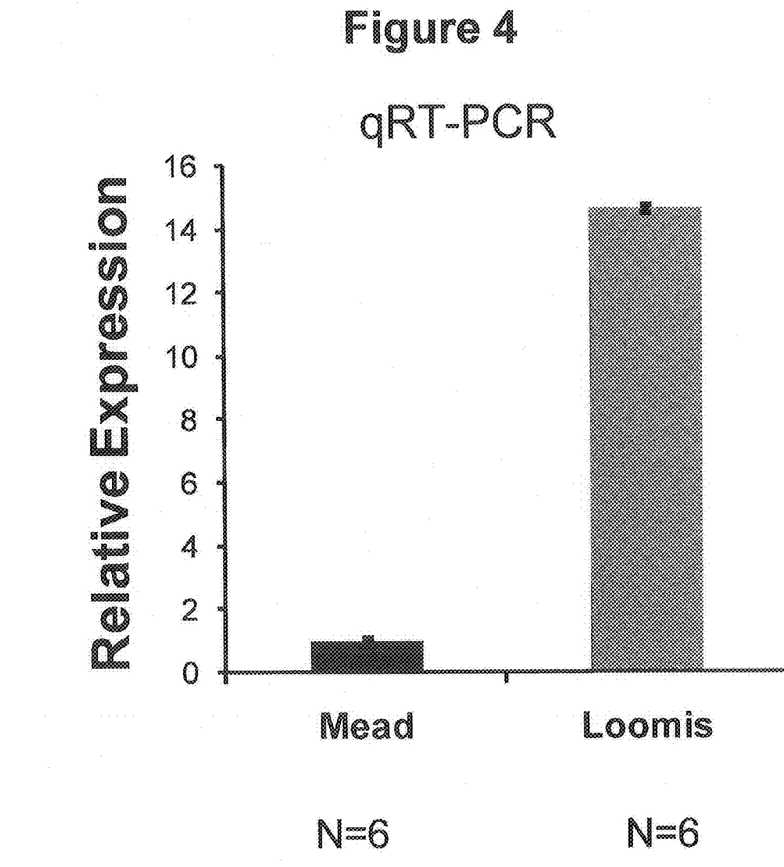
FIG. 4 shows the comparative expression of DvvEST3 as determined by qRT-PCR in the resistant Loomis population and the susceptible Mead population of western corn rootworms.
Figure 5:
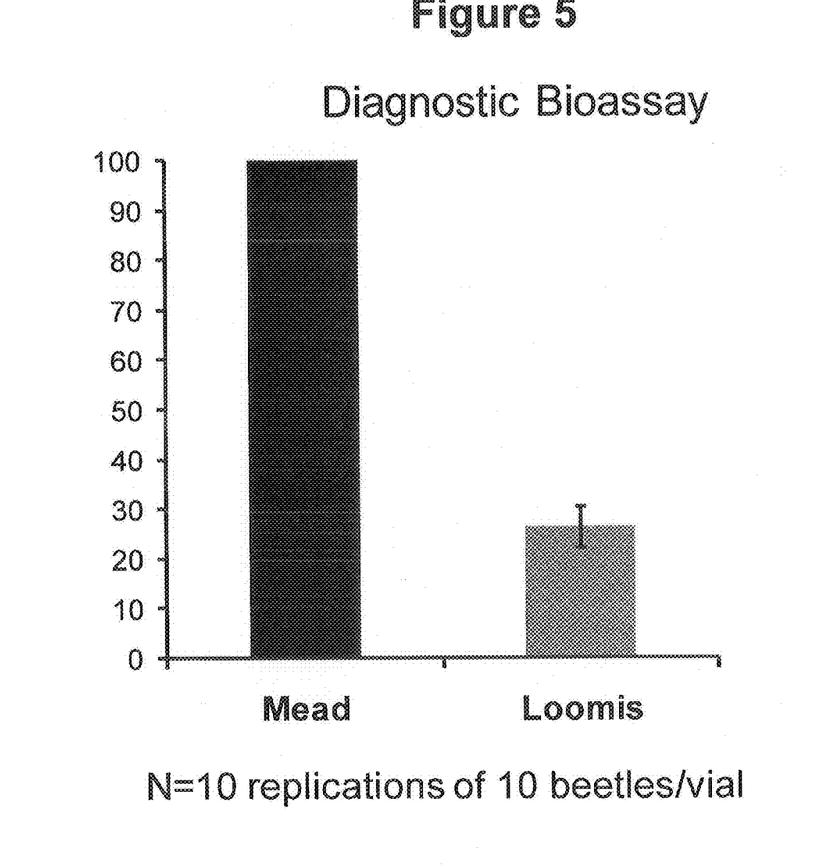
FIG. 5 shows the mortality of the resistant Loomis population and the susceptible Mead population of western corn rootworms as determined using a diagnostic concentration of methyl-parathion.
Figure 6:
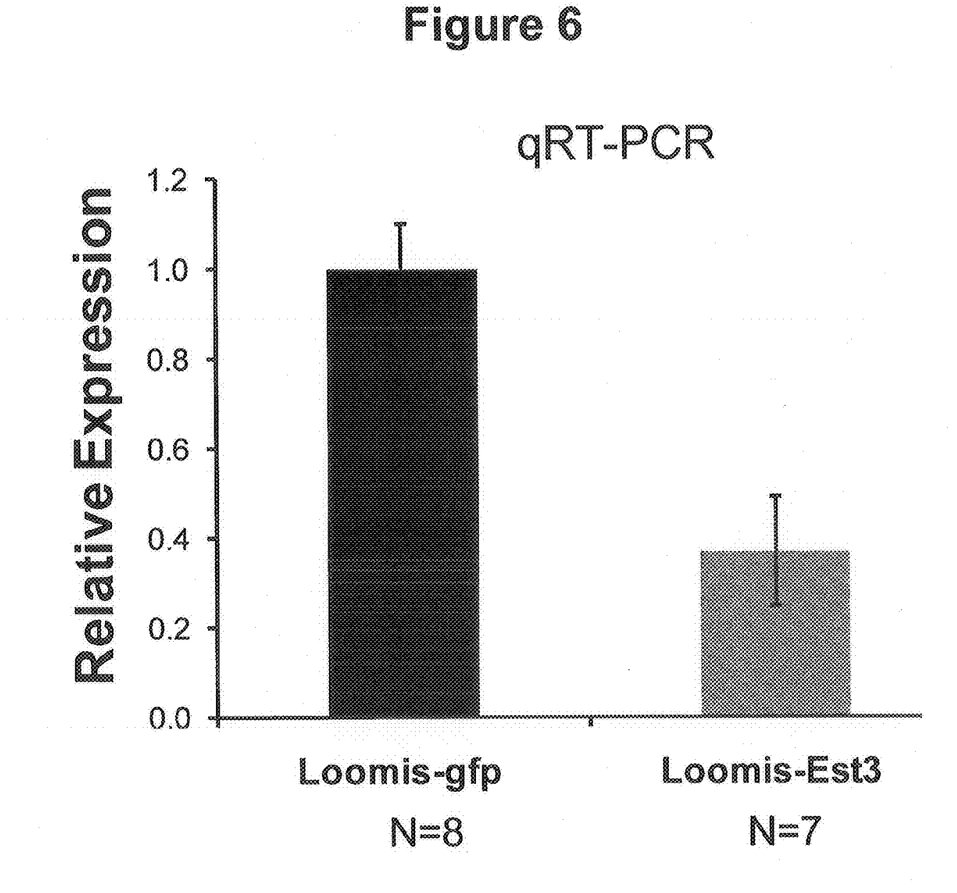
FIG. 6 shows the relative expression of DvvEST3 in a negative control treated with gfp-dsRNA compared to those treated with DvvEST3 ds-RNA.
Figure 7:
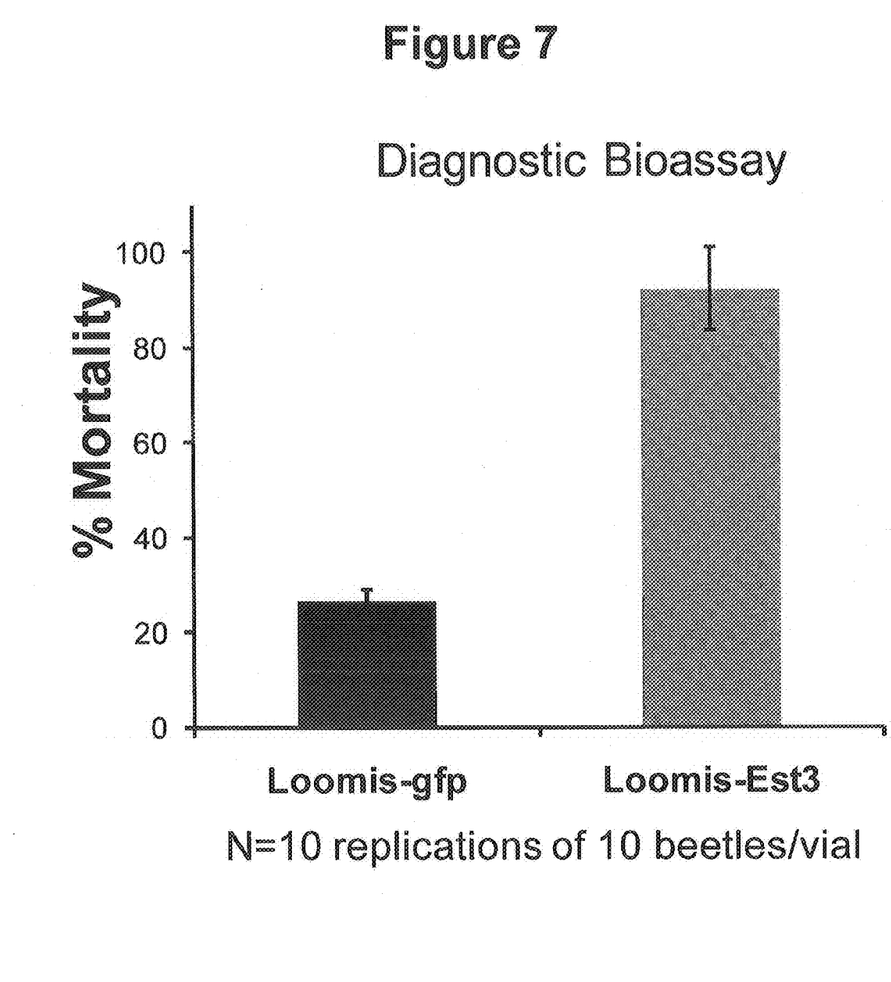
FIG. 7 shows susceptibility of the resistant Loomis population treated with DvvEST3 RNA or the negative control treated with gfp-dsRNA.

Western blot analysis of total protein from WCR adults showed reduced v-ATPase protein levels in vATPase-dsRNA fed WCR adults at 24, 48, and 72 hours after feeding (FIG. 2). The approximate size of putative WCR v-ATPase subunit A detected was ~68 kDa which is similar to the *Manduca sexta* v-ATPase subunit A (Graf et al., 1996; Merzendorfer et al., 2000).

3. Feeding bioassays with vATPase-dsRNA resulted in more than 95% WCR adult mortality within two weeks at both concentrations (500 and 1000 ng) which is significantly greater than either control (FIG. 3; F=32.38; df–4, 16; P<0.0001) in which mortality never exceeded more than 20%. Overall, no significant differences in mortality was observed between two vATPase-dsRNA concentrations tested (F=1.15; df=1, 16.5; P<0.2980) and between the water and gfp-dsRNA controls (F=0.01; df=1, 16.5; P<0.9290).

Feeding of vATPase-dsRNA resulted in drastic suppression of vATPase in adults with an average of 60, 86, and 84% at 24, 48, and 72 hours respectively after feeding (FIG. 1). In this example, although significant gene expression was observed within 3 days after feeding, the adult mortality was not significant until 6 days after feeding (FIG. 3).

V-ATPases are highly conserved ATP-dependent proton pumps present not only in intracellular organelles such as endosomes, lysosomes, and secretory vesicles in every eukaryotic cell but also found in the plasma membrane of many animal cells where they control cytoplasmic pH or energization of membranes (Beyenbach and Wieczorek, 2006; Nishi and Forgac, 2002; Wieczorek et al., 1999). Transgenic corn plants engineered to express the WCR putative vATPase-dsRNA showed reduced root damage and healthy root masses compared to control hybrid lines. Using a different strategy, (Mao et al., 2007) found that in planta expression of dsRNA in tobacco and *Arabidopsis* plants targeting CYP6AE14, a cytochrome P450 gene which is involved in detoxification of gossypol and highly expressed in midgut of *Heliothis armigera* larvae, caused reduction in expression of CYP6AE14 and increased susceptibility to gossypol (Baum et al., 2007). Baum et al. (2009) reported that constitutive expression of Cry3Bb1 and a 150-mer of dsRNA of putative WRC ESCRIII_Snf7 in corn plants showed reduced root damage rating when infested with WCR larvae and prevented adult emergence. Combined us of Bt toxins and RNAi in crop protection holds great promise for the future and can help the growers to cope up with development of Bt resistance in insect pests.

More recently, (Whyard et al., 2009) selectively designed and fed dsRNAs of subunit E of vATPase and observed larval mortality in *Tribolium castaneum, Manduca sexta, Drosophila* sp. and nymphs of *Aphis pisum* demonstrating species specificity of RNAi. Most of these studies used larvae or nymphs.

Example 2

Populations of western corn rootworms (WCR; *Diabrotica virgifera* virgifera) that display high levels of resistance to the organophosphate insecticide, methyl-parathion, have been shown to exhibit increased metabolism and increased esterase activity toward model substrates (Scharf et al. 1998, Zhou et al. 2003). A rootworm cDNA sequence has been identified with a high degree of similarity to other insect esterases known to be involved with insecticide resistance in other pest species. This gene was significantly over-expressed in a resistant population based on cDNA microarrays and confirmed by quantitative reverse transcriptase PCR (qRT-PCR). To confirm that this gene contributes to resistance to methyl-parathion, RNA interference was employed (RNAI) in which adult rootworms were fed double stranded RNA (dsRNA) to knockdown the expression of this gene and determine if the level of resistance was reduced in the treated insects.

Adult western corn rootworms were field collected in areas previously determined to be either susceptible (Mead) or resistant to methyl-parathion (Loomis). Over-expression of DvvEST3 for the susceptible and resistant populations was confirmed by qRT-PCR. The populations were also tested for susceptibility to methyl-parathion using a diagnostic bioassay (Zhou et al. 2001) to confirm resistance. Results of qRT-PCR and diagnostic methyl-parathion bioassays are presented in FIG. 4 and FIG. 5, respectively.

An artificial diet for WCR adults was prepared using a protocol modified from Nowatzki et al. (2006) and Jackson (1986). The diet consisted of 10% Invite EC (Florida Food Products, Eustis, Fla.) diluted in 4% agar, 0.32% methyl paraben, 0.12% sorbic acid, 0.16% streptomycin to minimize fungal and bacterial contamination, and 16.6% honey. The Invite EC contains a potent feeding stimulant for western corn rootworm adults (Nowatzki et al. 2006). Diet plugs (4 mm diameter×2 mm height) were made using a cork borer and treated with either DvvEST3-dsRNA or a non-specific negative control, green fluorescence protein (gfp)-dsRNA at 600 ng/plug. Mixed-sex adult rootworms were fed with artificial diet for 24 hours before initiating exposures to dsRNA. The WRC adults were provided with freshly treated diet plugs for 6 days.

The adults that were exposed to DvvEST3-dsRNA exhibited significantly reduced expression relative to the negative control treatment (gfp-dsRNA) as determined by qRT-PCR (FIG. 6). Additionally, the mortality at the diagnostic concentration of methyl-parathion increased significantly in the DvvEST3 treatment relative to the control (FIG. 7). These results confirm the involvement of DvvEST3 in resistance to methyl-parathion and support the utility of adult RNAi as a method to suppress gene expression in western corn rootworm adults.

Having illustrated and described the principles of the present invention, it should be apparent to persons skilled in the art that the invention can be modified in arrangement and detail without departing from such principles.

APPENDIX TO THE SPECIFICATION

TABLE 1

| |
|---|
| SEQ ID NO: 6 - Partial cDNA for Diabrotica virgifera virgifera vATPase (Accession number CN498337.1). |
| SEQ ID NO: 7 - Underlined region. |
| TAATCCAGACAGAGAAGGATCCGTTTCAATTGTAGGAGCCGTATCACC |
| TCCTGGTGGTGATTTCTCAGATCCTGTTACCACTGCTACTCTTGGTAT |
| TGTACAGGTGTTCTGGGGTTTGGACAAGAAACTTGCCCAACGTAAGCA |
| CTTCCCTTCAGTAGACTGGCTTGGATCATATTCCAAATATTTAAGAGC |
| ATTGGACGACTTTTATGACAAAAACTTCCAAGAGTTTATTCCTCTTAG |
| AACCAAAGTTAAGGAAATTCTTCAGGAAGAAGATGATCTAGCCGAAAT |
| TGTGCAGCTGGTAGGTAAAGCATCTCTGGCAGAAACGGACAAAATCAC |
| CTTGGAAATTGCCAGGCTTCTTAAAGAAGATTTCTTGCAACAAAACTC |
| ATACTCTTCTTATGACAGATTCTGTCCATTCTATAAAACTGTCGGTAT |
| GTTGAGAAACATGATCGGTTTGTACGACATGGCGAGACACGCTGTAGA |
| ATCAACCGCACAATCAGAAAATAAGATCACTTGGAACGTAATAAGAGA |
| TTCAATGAGTGGAATTTTATATCAACTTAGCAGTATGAAATTTAAGGA |
| TCCCGTAAAAGATGGTGAAGCTAAAATCAAGGCAGATTTTGATCAATT |
| ATATGAAGATATTCAGCAGGCCTTCAGAAACTTAGAAGATTAA |
| SEQ ID NO: 8 - cDNA for Diabrotica virgifera virgifera EST3. |
| SEQ ID NO: 9 - Underlined region. |
| ACACACGCTATAATTTGATCTTTGATCGGTCACAATGTTGTAGTGTTT |
| TTAGTTTATTGTGCCTCGAAGAGACAAAATCTAACCATGGCTCATGTG |
| GTGCAACTAGCGGAAGGAAAAATTTCTGGAGGCACTAGGACAGATCTC |
| AATGGGGATAAGTTTCATTCGTTTTTATGTATCCCATACGGAAAAGCT |
| CCAGTAGGCGACCTACGGTTTAAGGCGCCATTACCTGTTGAACCATGG |
| GAAGGGGTAAAACAAGTTATCACAGAAGACAAAACGCCATTCCAGAAG |
| AACATTGTTCTGAAGGAATATACTGGAGAAGAAGATTGCTTGTCTCTT |
| CATGTATTTACAAAGAAACTTCCCCATGAAGAATCCAAACTGAAACCT |
| GTGATGGTGTACATTCATGGAGGAGGTTTTATAATGGGATCTCACGAA |

TABLE 1-continued

```
ACTACGATGTATGGTCCAGAATACCTTATGACTGAAGACATAGTTCTC
GTAAGCATCACTTACCGAGTTGGTCTACTGGGTTTTCTTAGTATAGAA
GACGAATCACTGGACGTTCCTGGAAATGCAGGTCTAAAAGATCAAGTA
CTGGCTTTAAAGTGGGTCCAGCGAAACATAAGAAATTTCAATGGAGAT
CCCAATAACATTACCATATTTGGAGAAAGTGCGGGAGGGGCATCTGTT
GAATTTTTGCTGTTATCTCCTTCAGCCAAAGGTTTATTTCATAAAGCC
ATACTTCAGAGCGGGTCGACTTTAAATCCATGGACTCTTAAAAACTCC
CCAGCAACTGAGTTTGCTGAGTTTACCAAACTACATAACTTGCCTGAT
ATTGACATTTTGAAAAGCTTGAGGCGTATGACTGTTAGGGAGCTGTAC
GATCAACAAAATCAATATATTAAGTCTAAGAAGCTATTTGTAGATTTC
GGTCTAATAACCCCAGTGATAGAAAAACCCAACCCAACAGCATTTTTG
ACAGAGAAACCTATCGACATCATCCAGTCAGGGAAATACAACAATGTG
CCAGTGATAATGGGTTACACCGACAGTGAAGGTCTTCTTCTAGACTTC
TTGTCGGCACTTGGAATGAACGGGGCAAAAGAGGGAGAAGATATACCT
ATTGAGCAGATACTACCATACGAGACAAATTTAACAGATGCACAACAA
```

TABLE 1-continued

```
GTCAAACGATTAGTTGAAAAGTTAAGAAATTTTTATCGTCCAGAAGCT
GATCCGGTTGGACGAATTAATTTATCTACGGATGCCTTGTTTGCGGCT
GGAATAATCACTTCTGCAAAAAATCAAGCGAAAGTGTCAAAGAACCCT
GTATATTTTTATAGATTTTCATTGGACGCAGGCCTTAACATGCTGAAG
AAAATGGTGAATGATACACGTCCAGGAGCTTGTCACGGGGATGAACTG
GGATACCTATTTAAAAACCTTTTGACAACAGACATTGGAGATGAAGAT
AAAACTTATATACATCGAATGGTAACACTATGGACAAACTTTGCCAAA
TATGGAAATCCAACACCACCAGGAAATAATCTAAACATTGAATGGAAG
CCGATACAGAATGGTCAGTTGAATTTCTTAGATATTGGAAAACAACTA
AAGATGGATGTGAATCCAGACGCTGACAGGATGAAAATTTGGAATGAG
CTTTACCAGTGTAATCCACTGACAGCTAAATATTAAATTTGTTTGCAA
CAACTCTCAGAAATACATGTTATTATATTTTTATATTATAAAAAATAT
TTATATCATATTTTAAGACTATACGAATAAAACTGATTACTTTATTTT
AAAATAAAGTTACTACACAAAAA
```

What is claimed is:

1. A composition for delivering a dsRNA molecule to an insect, the composition comprising a cucurbitacin bait and at least one DvvEST3 dsRNA molecule, wherein the DvvEST3 dsRNA molecule elicits an RNAi response in the insect.

2. The composition of claim 1 wherein the composition comprises at least two dsRNA molecules of different sequences.

3. The composition of claim 1 wherein the composition further comprises a vATPase subunit A-dsRNA molecule that elicits an RNAi response in the insect.

4. The composition of claim 3 wherein at least one nucleic acid sequence selected from the group consisting of SEQ ID NO:6 and SEQ ID NO:7 is used as a template for synthesis of the vATPase subunit A-dsRNA molecule.

5. The composition of claim 1 wherein at least one nucleic acid sequence selected from the group consisting of SEQ ID NO:8 and SEQ ID NO: 9 is used as a template for synthesis of the DvvEST3 dsRNA molecule.

6. The composition of claim 1 wherein the composition comprises from about 5% to about 50% of the cucurbitacin bait.

7. The composition of claim 6 wherein the composition comprises from about 5% to about 25% of the cucurbitacin bait.

8. The composition of claim 6 wherein the composition comprises at least about 4% agar.

9. A method of delivering a dsRNA molecule to an insect, the method comprising providing an insect with a composition that comprises a cucurbitacin bait and at least one DvvEST3 dsRNA molecule to feed upon, wherein the DvvEST3 dsRNA molecule elicits an RNAi response in the insect and wherein the insect is selected from the group consisting of western corn rootworm, *Diabrotica balteata* LeConte, banded cucumber beetle, *Diabrotica barberi* Smith and Lawrence, northern corn rootworm, *Diabrotica undecimpunctata howardi* Barber, southern corn rootworm, and *Diabrotica speciosa*.

10. The method of claim 9 wherein the insect is a western corn rootworm.

11. The method of claim 9 wherein the composition comprises at least two dsRNA molecules of different sequences that elicit an RNAi response in the insect.

12. The method of claim 9 wherein the composition comprises about 5% to about 50% of the cucurbitacin bait.

13. The method of claim 9 wherein the dsRNA molecule increases mortality of the insect.

14. The method of claim 9 wherein the composition provided to the insect further comprises at least one vATPase subunit A-dsRNA molecule to feed upon that elicits a dsRNA response in the insect.

15. The method of claim 14 wherein at least one nucleic acid sequence selected from the group consisting of SEQ ID NO:6 and SEQ ID NO:7 is used as a template for synthesis of the vATPase subunit A-dsRNA molecule.

16. The method of claim 9 wherein at least one nucleic acid sequence selected from the group consisting of SEQ ID NO:8 and SEQ ID NO:9 is used as a template for synthesis of the DvvEST3 dsRNA molecule.

17. A method of producing a composition for delivering a dsRNA molecule to an insect, the method comprising combining a cucurbitacin bait and at least one DvvEST3 dsRNA molecule, wherein the DvvEST3 dsRNA molecule elicits an RNAi response in an insect.

18. The method of claim 17 wherein the composition comprises at least two dsRNA molecules of different sequences that elicit an RNAi response in the insect.

19. The method of claim 17 wherein at least one nucleic acid sequence selected from the group consisting of SEQ ID NO:8 and SEQ ID NO:9 is used as a template for synthesis of the DvvEST3 dsRNA molecule.

20. The method of claim 17 wherein the method further comprises combining a vATPase subunit A-dsRNA molecule that elicits an RNAi response in the insect with the cucurbitacin bait and at least one DvvEST3 dsRNA molecule.

21. The method of claim 20 wherein at least one nucleic acid sequence selected from the group consisting of SEQ ID NO:6 and SEQ ID NO:7 is used as a template for synthesis of the vATPase subunit A-dsRNA molecule.

22. The method of claim 17 wherein the composition produced comprises from about 5% to about 50% of the cucurbitacin bait.

* * * * *